United States Patent [19]

Rojey et al.

[11] Patent Number: 4,925,459
[45] Date of Patent: May 15, 1990

[54] PROCESS FOR SEPARATION OF THE CONSTITUENTS OF A MIXTURE IN THE GAS PHASE USING A COMPOSITE MEMBRANE

[75] Inventors: Alexandre Rojey, Garches; André Deschamps, Noisy Le Roi; Alain Grehier, Paris; Eric Robert, Rueil-Malmaison, all of France

[73] Assignee: Institut Francais Du Petrole, Rueil-Malmaison, France

[21] Appl. No.: 295,316

[22] Filed: Jan. 10, 1989

[30] Foreign Application Priority Data

Jan. 11, 1988 [FR] France ................ 88 00243

[51] Int. Cl.$^5$ .................. B01D 53/22; B01D 53/04
[52] U.S. Cl. .................. 155/16; 55/68; 55/75; 55/158; 55/389; 585/818
[58] Field of Search .......... 55/16, 68, 158, 75, 55/387, 389; 585/818, 819

[56] References Cited

U.S. PATENT DOCUMENTS

| | | | |
|---|---|---|---|
| 2,924,630 | 2/1960 | Fleck et al. | 55/16 X |
| 2,983,767 | 5/1961 | Fleck et al. | 55/16 X |
| 3,241,293 | 3/1966 | Pfefferle | 55/16 |
| 3,567,666 | 3/1971 | Berger | 55/16 X |
| 3,709,774 | 1/1973 | Kimura | 55/16 X |
| 3,911,080 | 10/1975 | Mehl et al. | 55/16 X |
| 4,208,194 | 6/1980 | Nelson | 55/389 X |
| 4,230,463 | 10/1980 | Henis et al. | 55/16 |
| 4,261,832 | 4/1981 | Schumacher et al. | 55/16 X |
| 4,318,714 | 3/1982 | Kimura et al. | 55/16 |
| 4,329,157 | 5/1982 | Dobo et al. | 55/16 |
| 4,740,219 | 4/1988 | Kulprathipanja et al. | 55/16 |

FOREIGN PATENT DOCUMENTS

| | | | |
|---|---|---|---|
| 0154248 | 9/1985 | European Pat. Off. | |
| 0254758 | 2/1988 | European Pat. Off. | |
| 2079460 | 11/1971 | France | |
| 55-119418 | 9/1980 | Japan | 55/158 |
| 60-135434 | 7/1985 | Japan | 55/158 |
| 60-153903 | 8/1985 | Japan | |
| 61-035808 | 2/1986 | Japan | 55/158 |
| 61-138516 | 6/1986 | Japan | 55/158 |
| 1247992 | 9/1971 | United Kingdom | |
| 2005016 | 4/1979 | United Kingdom | 55/158 |
| 2143772 | 2/1985 | United Kingdom | 55/158 |
| 2159133 | 11/1985 | United Kingdom | 55/158 |

OTHER PUBLICATIONS

Hennepe et al., J. of Membrane Science 35 (1987), Dec. 15, No. 1, pp. 39–55.

Primary Examiner—Robert Spitzer
Attorney, Agent, or Firm—Millen, White & Zelano

[57] ABSTRACT

A mixture of at least two constituents A and B is submitted to selective separation across a selective membrane.

The membrane comprises an active layer comprising particles of a selective solid (5) dispersed in a continuous non-porous and non-elastomeric polymer phase (4) and a porous support (6). The thickness of the active layer is less than 100 micrometers, advantageously less than 20 micrometers.

31 Claims, 2 Drawing Sheets

PROCESS FOR SEPARATION OF THE CONSTITUENTS OF A MIXTURE IN THE GAS PHASE USING A COMPOSITE MEMBRANE

BACKGROUND OF THE INVENTION

The invention concerns a process for separation of the constituents of a mixture in the gas phase using a composite membrane comprising an adsorbent and, in particular, to the separation of a mixture comprising hydrocarbons.

Separation processes using membranes and gas permeation processes in particular have recently undergone great advances due to the development of asymmetric membranes whose active layer is very thin and of hollow fiber modules with large specific surfaces.

Nonetheless, these processes, which already have commercial applications, for example, in the separation of hydrogen from a gaseous mixture of hydrogen and hydrocarbons or in the separation of carbon dioxide from a gaseous mixture of carbon dioxide and hydrocarbons, have not yet led to results in the field of separation of hydrocarbon isomers.

In fact, the polymer-based membranes which have been developed so far do not show sufficient selectivity for the separation of isomers such as normal paraffins/isoparaffins, meta and paraxylene, olefins/paraffins.

The composite membranes according to previous techniques involve a superposition of parallel layers formed from materials with differing properties, according to the diagram in FIG. 1 in which these parallel layers (1, 2, 3) are represented.

For example, U.S. Pat. No. 4,230,463 describes how a very permeable and not very selective silicone membrane can be superimposed on an active polysulfone layer in order to improve performance, thus allowing reduction of the microfissure effect in the active polysulfone layer.

According to this principle, use of a composite membrane comprising an active layer consisting of a material such as a zeolite has already been suggested in European patent EP-0810200.

In practice, it is nonetheless difficult to make up a crystalline layer from a material such as a zeolite that is sufficiently fine and uniform.

European patent No. 0180200 points out that in order to make up such a selective layer by impregnation, trapping zeolite particles in the pores of the porous medium, the pores must be sufficiently well-calibrated and the particles must have a relatively uniform dimension. This is also the case in U.S. Pat. No. 3,567,666 which describes a porous, polymer-based structure whose channels contain molecular sieve microporous particles, the pores of these particles being interconnected by the channels.

These methods encounter numerous difficulties: difficulty in calibrating the pores of the porous support and the zeolite particles, in controlling the thickness of the zeolite film and in preparing a continuous layer.

Moreover, it can be difficult to carry out various treatments after trapping particles, particularly if the porous support is polymer-based and if the treatment necessitates high temperatures.

FR patent No. 2,079,460 describes a membrane consisting of (a) a polymer, (b) a zeolite dispersed in the polymer and (c) a strengthening support such as a polyester or a polyamide. The thickness of membranes obtained in this way is between 100 and 1000 micrometres.

Due to this, diffusion of the product that is passed across the membrane is low and the rate of flow of products are reduced. We are thus led to increase the difference in pressure between faces of the membrane in order to obtain an acceptable outlet flowrate. However, this leads to an increased cost in materials as well as an equally costly consumption of energy and an increased risk of membrane rupture.

A membrane comprising a polymer matrix consisting of a silicone (silicone rubber) or polyisoprene-based elastomer, in which a zeolitic material is dispersed, is described in the patent EP-A-0.254.758 and in the document "Journal of Membrane Science vol. 35, n. 1, Dec. 15, 1987, pages 39–55, Elsevier Science Publishers B. V. Amsterdam".

Further, a membrane comprising functional groups or zeolites chemically grafted onto polymer molecules is described in the patent EP-A-0.154.248.

Moreover, previous techniques illustrated by U.S. Pat. No. 2,924,630 describe a separation process using membranes containing zeolites whose pore diameters are between 3 and 15 Angströms. Such techniques are also described in the document Chem. Abstract, Volume 85, 1976 n. 1, page 410, n. 5102Z, which describes a molecular sieve membrane used for separation of methane and lower olefins.

Finally, previous techniques are illustrated by the document Patent Abstract of Japan, volume 9, n. 317 (2040), 12 Dec. 1985 which describes a membrane with silica whose surface is treated with a binding agent and by FR patent No. 2011125 where the membrane only comprises one layer of granules imbedded partially in a plastic sheet.

It has been discovered that separation of hydrocarbon isomers becomes possible if a new membrane is formed.

Furthermore, the process according to the invention allows separation of gaseous mixtures, such as hydrogen/methane and methane/$CO_2$, to be carried out under more favorable conditions.

The membrane used according to the invention is a composite membrane incorporating a selective adsorbent phase vis-a-vis one of the constituents present in the mixture to be separated.

SUMMARY

The principle for shaping the membranes used in the process according to the invention is different and will be better understood with reference to the following figures:

Figure 1:
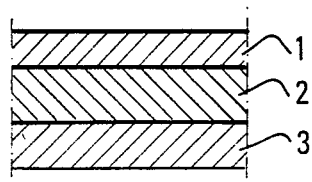
FIG. 1, as mentioned hereinabove, represents a composite membrane according to previous techniques.

It has been discovered that by dispersing the particles of a selective adsorbent phase in a continuous and non porous polymer, and as long as the conditions mentioned below are satisfied, it is possible to prepare a selective composite phase without the above-mentioned inconveniences and with improved effectiveness.

Another objective of the invention concerns the process for obtaining a very thin asymmetric membrane and concerns the membrane so obtained.

Another objective concerns a process for enrichment in iso-alkanes combining a step of isomerization of a n-alkane cut followed by a step of separation of n- and iso-alkanes.

The membrane used in the process according to the invention (FIG. 2) is thus composed of at least one active layer comprising a continuous polymer phase (4) and particles (5) of the dispersed adsorbent phase and a porous support layer (6).

In the active layer, the particles of the selective adsorbent phase are dispersed uniformly on the whole thickness of the selective layer and are not on the surface. The continuous phase forms a dense film without porous structure in the range of the particles.

Transfer of a constituent across a selective membrane necessarily implies permeation of said constituent across the continuous phase by a sorption mechanism in the material forming the continuous phase then by diffusion in said material. The presence of the dispersed phase may contribute either to accelerate or slow down the transfer of a constituent across the selective layer, depending on whether permeation of said constituent across the dispersed phase is quicker or slower than across the continuous phase.

It was thus discovered that it is possible to shape an active, permeable and selective layer by associating, under the conditions which are the subject of a more detailed description of the process, a selective dispersed phase with a continuous permeable but non selective phase.

The process according to the invention comprises the following steps: (a) a mixture of at least two constituents A and B in the gas or vapor phase is contacted with the first face of a membrane composed of (i) at least one active layer comprising a solid adsorbent phase, selective vis-a-vis constituent A, dispersed in a substantially uniform manner in a non elastomeric non porous polymer and constituting a continuous phase and (ii) a porous layer acting as a support, (b) the partial pressure of constituent A is kept lower at the second face of the membrane than at its first face and a mixture enriched in constituent A and impoverished in constituent B is collected at the second face of said membrane, and (c) a mixture enriched in constituent B and impoverished in constituent A is collected at the first face of the membrane. Steps (a), (b) and (c) are preferably carried out successively.

By a non porous polymer, we mean a polymer across which migration of products is carried out mainly by molecular dissolution and diffusion. Transport in the polymer between zeolite particles which may be submitted to a Knudsen type law are excluded from this definition.

More accurately, the thickness of the active layer is less than 100 micrometers, for example, from 0.1 to 90 micrometers. It is thus sufficiently permeable vis-a-vis constituent A. More advantageously, thickness is less than 20 micrometers. With a preferred thickness of less than 1 micrometer, transfer kinetics are greatly improved, notably with thicknesses from 0.1 to 0.5 micrometers.

The average dimension of the particles constituting the dispersed adsorbent phase is generally less than 25 micrometers and advantageously less than 7.5 micrometers. With a preferred average particle size less than 0.1 micrometer, for example, from 200 to 900 Angströms (1 Angström=$1\times10^{-10}$m), we obtained excellent separation results and, in particular, with an average particle size less than 500 Angströms.

The process according to the invention has the advantage of a greater efficiency in separation and is easier to implement.

In order to obtain particles with a dimension greater than about 1 micrometer, we can resort to conventional means such as grinding and sieving. On the other hand, in order to obtain particles with a dimension less than 1 micrometer, we modify, for example, the synthesis conditions of the zeolite concerned in such a way that the nucleation is favorized rather than the crystallite growth process, for example. In order to attain this objective, we can either reduce the synthesis temperature or we can operate under conditions of compound supersaturation or we can limit reaction time.

The thickness of the active layer can be controlled in the following manner:

for thickness between 1.0 and 100 micrometers for for example, macroscopic measurement means such as a micrometer gage or a comparator can be used.

For thicknesses between 0.1 and 10 micrometers for example, a micrographic technique can be used or this thickness can be deduced from measurement of the rate of flow of a defined gas such as hydrogen or helium across the surface of a membrane known to have a determined difference in pressure on both faces of the membrane that is thick enough to be measured by conventional means such as those described hereinabove.

Figure 3:
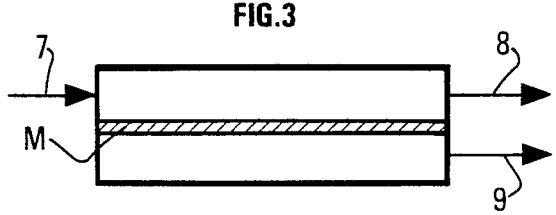
FIG. 3 illustrates the separation process according to the invention.

The principle of the process according to the invention is illustrated by the diagram in FIG. 3.

Figure 2:
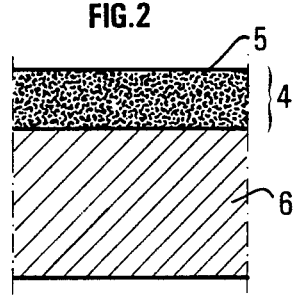
FIG. 2 illustrates the principle for shaping the membranes used in the process according to the invention.

A mixture comprising at least two constituents A and B to be separated arrives by pipe 7 and circulates on one side of the membrane M prepared according to the diagram of the principle given in FIG. 2.

The mixture is in the gas or vapor phase and constituent A selectively passes across the membrane M under the effect of the difference in partial pressure.

The mixture enriched in constituent A is evacuated by the pipe 9 and the mixture impoverished in constituent A, and thus enriched in constituent B, is evacuated by the pipe 8.

In order to operate the process according to the invention, as has been indicated, it is necessary to respect certain conditions.

In order to obtain a sufficiently homogeneous active layer, the dimension of the particles of the dispersed phase is preferably sufficiently small with respect to the thickness of the active layer, the ratio of the average size of particles of the dispersed phase to the thickness of the active layer preferably being less than 0.25, for example between 0.1 and 0.25.

Very fine particles such as this can be obtained by ultrafiltration of a crystal suspension for example.

The ratio of the dispersed adsorbent phase mass to the continuous polymer phase mass must be sufficiently high and advantageously greater than 1, for example, 1/1 to 1/10, and preferably, 2/1 to 6/1.

Due to its thickness the active layer should be deposited on at least one porous layer to which it adheres with sufficient mechanical resistance.

This support layer, in order to be sufficiently permeable, is generally macroporous, that is to say it has pores whose diameters are in the range of particles of the dispersed phase, for example, greater than 25 micrometers.

It can consist of either a porous material or another material, for example, a sintered metal plate or a sintered mechanism.

The adsorbent phase should be selective vis-a-vis constituent A.

Molecular sieves formed by different natural or synthetic zeolites are already used to carry out selective separations of constituents which differ in molecule size or in their chemical affinity. Nonetheless, their use in fixed beds necessitates a discontinuous operation and complex use of valves, which may be avoided by the process according to the invention.

Various types of molecular sieves can be used to form the phase dispersed in the non porous polymer of the membrane used in the process according to the invention.

Thus, for example:

The KA type zeolite a.k.a. molecular sieve 3 A, allows a constituent whose molecule has a size less than 3 Angströms (1 Angström=$1 \times 10^{-10}$m) to be separated from a constituent whose molecule has a size greater than 3 Angströms. It thus allows separation, for example, of the water which passes through the pores of the zeolite and methane which is excluded, to be carried out.

The NaA type zeolite, a.k.a. molecular sieve 4 A, allows a constituent whose molecule has a size less than 4 Angströms to be separated from a constituent whose molecule has a size greater than 4 Angströms.

The CaA type zeolite, a.k.a. molecular sieve 5 A, allows normal paraffins to be separated from a mixture of normal paraffins and isoparaffins.

K-BaY, Sr-BaX, K-BaX and ZSM5 zeolites allow paraxylene to be separated from a mixture of paraxylene, metaxylene, orthoxylene and ethylbenzene. NaY and Sr-KX zeolites allow ethylbenzene to be separated from a mixture of ethylbenzene, orthoxylene, metaxylene and paraxylene.

Zeolites such as CaX and SrX allow olefins to be separated from a mixture of olefins and paraffins.

Zeolites are thus particularly adapted for the use in the formation of the phase dispersed in the selective layer of the membrane used in the process according to the invention.

Nonetheless, other materials can also be used. For example, we know how to shape carbon-based molecular sieves having pores of calibrated size which can also be used as a dispersed phase. Divided particles of activated charcoal can also be used.

In some cases, selective adsorbent phases which are not molecular sieves can also be used, for example, some ion-exchange resins.

The materials that can be used to prepare the active layer will be thermoplastic or thermosetting type non elastomeric polymers. Among the usual technical polymers, charged or uncharged materials that are effective at high temperatures are preferably be used. We can cite the following as examples: among the thermoplastic polymers:

(a) the polysulfone family (phenylene polysulfide, polyarylsulfone, polyethersulfone),
(b) the ketone family (polyetheretherketone, polyetherketone),
(c) polyetherimides,
(d) polyamide-imides,
(e) ionomer resins,
(f) thermoplastic polyimides,
(g) fluorinated polymers.

Among the thermosetting polymers, other than conventional polyester resins and epoxides, silicone resins and polyimides can be used. Copolymers can also be used.

Polyimides are preferably used. We can thus operate at relatively high temperatures, above 100° C. for example, which improves the transfer kinetics across the membrane.

Concerning the porous support layer, polymers of the same type as those constituting the active layer are preferably used. Sintered metals such as stainless steels, nickel or sintered ceramics can also be used.

The diameter of the pores of this support layer is generally between 3 and 100 micrometers.

In order to obtain an active membrane layer having a thickness defined according to the invention, we can for example:

for thicknesses over 20 micrometers, use the technique described in the patent FR No. 2.079.460, with the products in proportions according to the invention;

for thicknesses below 20 micrometers, and in particular to obtain an active layer of a thickness less than 1 micrometer, we can coagulate an active layer which constitutes the selective layer of the membrane, by contacting an anti-solvent with one face of a film consisting of a non elastomeric polymer in solution in a solvent containing the dispersed adsorbent phase for a period from 1 to 24 hours and at a temperature usually between $-20°$ C. and $+100°$ C. The temperature is generally chosen as a function of the polymer solvent. We thus obtain at this face of the film the active layer comprising the dispersed adsorbent phase in a non-porous polymer phase and an underlying porous polymer phase undissociated of the active layer which constitutes the support layer.

By undissociated, we mean that the active layer and the support layer are interdependent and only differ in their respective structures, the polymer constituting the two layers being the same polymer but said polymer having a continuous structure in the active layer and a porous structure in the support layer, both layers containing the adsorbent phase dispersed in a substantially homogeneous manner in the polymer.

According to another characteristic of the process for preparing the membrane, the polymer film can be deposited on a support, preferably porous, for example, a sintered metal plate.

Various solvents can be used to solubilize the polymer, either light solvents with relatively low boiling points such as dichloromethane, or heavy solvents with relatively high boiling points such as N-methylpyrrolidone.

The coagulating agent that leads to precipitation of the polymer by forming a very thin active layer on the surface acts as an anti-solvent vis a vis the polymer and can be, for example, water or even a polar organic solvent such as acetone.

More complex mixtures can also be used and the various methods known to a person skilled in the art for preparing an asymmetric membrane from a polymer material can be employed. The essential condition for preparing a membrane according to the process consists of putting particles of the dispersed phase in suspension in the polymer solution, respecting the conditions mentioned.

Dispersion of zeolite particles and the stability of the suspension can be improved by addition of a surfactant soluble in the polymer solvent.

We can also carry out pretreatment of the dispersed phase with a binding agent such as a silane before mixing it with the polymer solution. According to another procedure, the binding agent can be incorporated into the polymer solution before introduction of the dispersed phase. These two procedures allow the binding agent to be introduced at the interface between the dispersed phase and the continuous phase thus ensuring better adhesion of the two phases.

The process according to the invention leads to appreciable improvement in the separation of gaseous mixtures by gaseous permeation each time the adsorbent used allows preferential passage of one of the constituents present in the mixture.

The membranes are generally used in the form of an even sheet.

Other geometries can also be envisaged. It is possible to roll the membranes in the shape of a spiral in order to obtain more compact separation device.

It can also be advantageous to put the membranes in hollow fiber form of a diameter less than 5 mm in order to increase the specific exchange surface. These hollow fibers are obtained by extrusion of a die across an orifice followed by immersion of the hollow fiber in an antisolvent bath. We thus obtain a very thin selective layer, supported by a macroporous structure.

Transfer of constituent A across the membrane can be carried out under appreciably isothermal conditions.

The temperature at which this transfer is carried out is preferably between 30° and 150° C.

The following examples illustrate the invention.

EXAMPLE 1 (comparative)

(a) A membrane is prepared according to previous techniques as follows:

A solution a comprises in 25 parts in weight of polyetherimide (Trademark: ULTEM dissolved in 100 parts in weight of n-methylpyrrolidone (NMP).

After controlled evaporation of the solvent under nitrogen at 130° C. until a product with a viscous consistency is obtained, the latter is coated onto class 05 sintered stainless steel of a thickness of 1 mm in a uniform manner in order to obtain a film with a thickness of 0.15 mm, after evaporation of the solvent. Evaporation of the solvent is obtained by progressive heating from 50° to 200° C. at atmospheric pressure, followed by 24 hours at 200° C. and passage under vacuum at this temperature for 24 hours.

(b) separation:

An equimolar mixture of hydrogen and methane is introduced under a pressure of 60 bars by a pipe 7 (FIG. 3) at a flow rate of 1 m$^3$/h measured under normal conditions of temperature and pressure. The high- and low-pressure compartments ($\Delta P = 30$ bars) are separated by the above membrane of a surface of 1 m$^2$. They are maintained at a temperature close to room temperature. 0.35 g/h of hydrogen and 0.002 g/h of methane are evacuated by a pipe 9.

EXAMPLE 2 (comparative)

(a) 12.5 parts in weight of zeolite 4 A consisting of particles whose average size is less than 1 micrometer, are maintained at 350° C. for 24 hours under a vacuum of $10^{-3}$ torr.

After cooling down under vacuum, 100 parts in weight of NMP are added under vacuum. The zeolite 4 A-NMP mixture put back under atmospheric pressure constitutes suspension B. Solution A is prepared by putting 11 parts in weight of polyetherimide ULTEM in solution in 45 parts in weight of NMP. After stirring, suspension B is mixed with solution A. The mixture is then maintained under nitrogen at 130° C. until evaporation of about half the NMP occurs, in order to obtain a product of a viscous consistency.

(b) The mixture is coated onto class 05 sintered stainless steel with a thickness of 1 mm in a uniform manner in order to obtain a film with a thickness of 0.15 mm after evaporation of the solvent, as in example 1a. Separation is carried out according to example 1b and 3.1 g/h of hydrogen and 0.004 g/h of methane are recovered by a line 9.

EXAMPLE 3

Example 3 is carried out according to steps 2a and 2b of example 2 but evaporation of the film is controlled in a way such that an active layer with a thickness of about 70 micrometers is obtained. 9 g/h of hydrogen and 0.003 g/h of methane are evacuated, operating according to the conditions set forth in example 2.

EXAMPLE 4

Example 4 is carried out according to step 2a of example 2, except that the particles used have an average size less than 500 Angströms (1 Angström $= 1 \times 10^{-10}$ m).

The viscous mixture is coated onto a glass plate under nitrogen using a scraper in such a way as to obtain a uniform film of about 100 micrometers in thickness. After 10 minutes under nitrogen, the glass plate-film system is immersed for 16 hours in a distilled water bath at room temperature, serving as a coagulating agent.

The thickness of the active layer obtained in this way, deduced from measurements of gas flow rate (He) and permeability, is estimated at 0.8 micrometer.

After separation by the membrane obtained in this way according to example 1b, 1020 g/h of hydrogen and 0.32 g/h of methane are evacuated.

It can be observed that it is possible in this case, with the same membrane surface, to produce a greater rate of flow of purified hydrogen at the same time as allowing less methane to pass through.

EXAMPLE 5

The same process can be used to separate water and methane in the gas phase, using a polymer-based membrane, for example polyetherimide, and a type 3 A molecular sieve which allows water to pass and stops methane, under the conditions defined in examples 3 and 4.

It is possible to dehydrate a natural gas in this way until very low contents in water are obtained, for example less than 5 ppm in volume, provided the side of the membrane where the water is withdrawn is drawn under vacuum in order to maintain a partial pressure of water at the side where the water is withdrawn that is less than the partial pressure of the water in the gas at the side where the dehydrated gas is withdrawn.

EXAMPLE 6

An equimolar mixture of normal pentane and isopentane is prepared:

190.4 g/h of the mixture in the liquid phase is removed by a pump P1 (FIG. 4) and is introduced by a pipe 20 into the exchanger EV1, from where it immerges in the vapor phase at a temperature of 100° C. This vapor phase (21) is introduced by pipes 22 into 26 to a permeator 60 with level plates 61. In order to simplify the diagram, the exact number of plates has not been represented. We work with 100 plates of 1.6 m² each. Each plate consists of a membrane comprising an active layer on a sintered metal porous support. The membrane was obtained by spreading out on a sintered metal porous support of 5 mm in thickness a film consisting of a suspension of a 5 A molecular sieve, whose crystallites have an average dimension of 0.1 μm, in a solution of ULTEM-type polyetherimide in dichloroethane, the ratio of sieve mass to total sieve and polyetherimide mass being 0.8. After evaporation of the solvent, a film of a thickness of about 10 micrometers is obtained.

A vapor phase enriched in isopentane is withdrawn by pipes 27 to 31. It has the following molar composition:
$iC_5$: 0.987
$nC_5$: 0.013

The gaseous mixture obtained in this way is evacuated by a pipe 32 and passes through the relief valve V10, which allows a controlled and constant pressure of 4.5 bars to be maintained in pipes 27 to 31. The expanded mixture is introduced by a pipe 33 into condenser EC1, from which it emerges by a pipe 34, the mixture in the liquid phase being collected in a flask B1 from which it is evacuated by a pump P2.

A total rate of flow of 98.7 g/h of a vapor phase enriched in normal pentane is withdrawn by pipes 35 to 39. It has the following molar composition:
$iC_5$: 0.952
$nC_5$: 0.048

The vacuum pump PV2 allows a pressure of 0.6 kPa to be maintained in pipes 35 to 39. At the outlet of the vacuum pump PV2, the vapor mixture is introduced by a pipe 40 into a condenser EC2, from which it emerges by a pipe 41. The mixture in the liquid phase is collected in a flask B2, from which it is evacuated by a pump P3.

EXAMPLE 7

Figure 4:
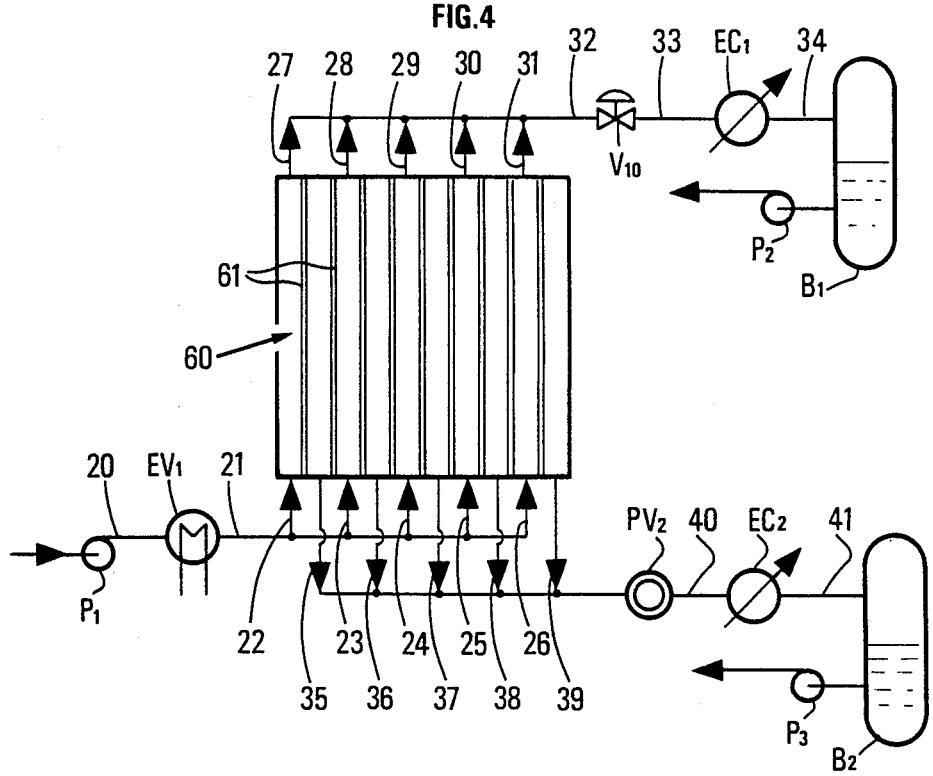
FIG. 4 shows a diagram for the separation of a mixture of normal pentane and isopentane.

We work with the same mixture as in example 6 and the same device consisting of 100 plates of 1.6 m², represented in the diagram in FIG. 4.

Nonetheless in this case, preparation of the membrane was modified and the technique used consists of preparing as asymmetric composite membrane.

In order to obtain an even membrane such as this, a solution of polyetherimide (marketed under the name of ULTEM), in a mixture containing 80% in weight of dichloromethane, 5% in weight of trichloroethane and 10% in weight of xylene is prepared. The solution contains 25% in weight of polyetherimide. This solution was charged with particles of a 5 A sieve of an average size less than 250 Angströms (1 Angström = $10^{-10}$m) in such a way as to obtain a suspension containing 50% weight in sieve.

The polymer solution charged in this way is then spread out on an even sintered metal plate using an applicator.

Partial evaporation of the solvent is carried out for 15 seconds at a temperature of 20° C. under dry nitrogen sweeping. Coagulation of the polymer is then carried out by contacting the charged polymer film with acetone at 20° C. for one hour. The plate is dried in the oven at 100° C. for 4 hours then submitted to thermal treatment under vacuum at 180° C. for 4 hours.

It is observed that by using the same device as in example 6, it is possible in this case to considerably increase the rate of transfer across the membrane.

After adaptation of pumps P1, P2, P3 and exchangers EV1, EC1 and EC2 as well as vacuum pump PV2, a flow rate of 17.2 kg/h of the mixture in the liquid phase is sent by the pump P1. After vaporization in the exchanger EV1, this vapor phase is sent to a permeator by pipes 22 to 26.

A total flow rate of 8.3 kg/h of a vapor phase enriched in isopentane is withdrawn by pipes 27 to 31. It has the following molar composition:
$iC_5$: 0.988
$nC_5$: 0.012

The gaseous mixture is maintained at a controlled pressure of 4.5 bars, at the level of pipes 27 to 31, with a relief valve V10. At the outlet of the relief valve V10, the mixture is condensed in a condenser EC1 and evacuated by a pump P2.

A total flow rate of 8.9 kg/h of a vapor phase enriched in normal pentane is withdrawn by pipes 35 to 39. It has the following molar composition:
$iC_5$: 0.955
$nC_5$: 0.045

The vacuum pump PV2 allows, as in example 2, a pressure of 0.6 kPa to be maintained at the level of pipes 35 to 39.

In examples 6 and 7, the difference between the equilibrium in the partial pressures of constituent A on the one hand, and the membrane on the other hand, is effected by drawing under vacuum the side of the membrane where constituent A is withdrawn.

It is also possible to effect this difference in the equilibrium of partial pressures by circulating an eluent at the side of the membrane where constituent A is withdrawn.

Figure 5:
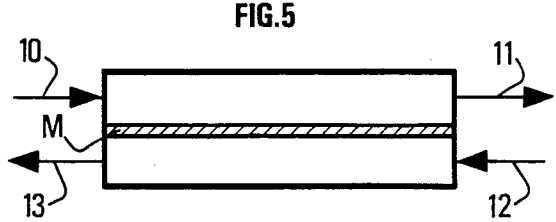
FIG. 5 represents the separation process according to the invention in which the partial pressure of the constituent that is to cross the membrane is reduced by circulation of a gaseous eluent at the side where this constituent is withdrawn.

In this case, we can operate according to the diagram illustrated in FIG. 5.

The mixture to be separated arrives in the gas phase by a pipe 10. The gaseous eluent arrives by a pipe 12. This allows reduction of the equilibrium partial pressure of constituent A and transfer of constituent A across the membrane. The mixture enriched in constituent A emerges by a pipe 13, and the mixture enriched in constituent B emerges by a pipe 11.

The eluent can comprise nitrogen and hydrogen for example.

Thus, in the case of separation of a mixture of normal paraffins and isoparaffins, for example, it can be particularly advantageous to use hydrogen as an eluent when the separation process is coupled with an isomerization process, operating in the presence of hydrogen.

Figure 6:
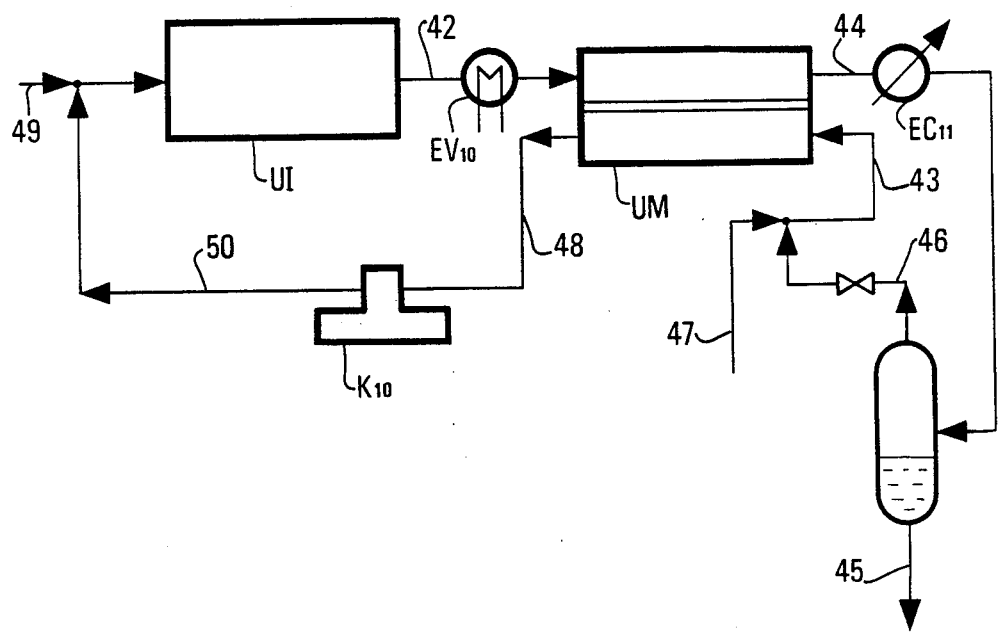
FIG. 6 shows the coupling of an isomerization process with a separation process.

In this case, we can proceed according to the layout illustrated by the diagram in FIG. 6.

An equimolar mixture of isopentane and normal pentane in the gas phase is admitted, under a pressure of 20 bars at a temperature of 250° C. by a line 49, into the isomerization unit UI in mixture with a recycling stream containing 90% in volume of hydrogen and 10% in volume of normal pentane, arriving by a line 50.

The mixture which emerges in the gas phase from the isomerization unit UI at a temperature of 280° C. by a pipe 42 contains a normal pentane fraction, expressed in mass with respect to the mass of total normal pentane and isopentane equal to 20%. The mixture is then cooled down in the exchanger EV10 from which it is sent, in the gas phase, to a separation device UM equipped with asymmetric composite membranes prepared according to the process described in example 7. The mixture, enriched in normal pentane, which has crossed the membrane is eluted by hydrogen which arrives by pipes 47 and 43. The mixture enriched in isopentane, which emerges by a pipe 44 of the separation device UM, contains hydrogen which is transferred across the membrane and a mixture of normal pentane and isopentane containing about 2% of normal pentane with respect to the mass of total normal pentane and isopentane. After cooling down to about 30° C. in an exchanger EC11, the the isopentane-rich fraction of the mixture is condensed then evacuated by a pipe 45. The gas phase (46) joins the hydrogen stream (47). The hydrogen and normal pentane mixture (48) is compressed (K 10) and recycled in the isomerization unit.

What is claimed is:

1. Process for separation of a mixture of at least two constituents A and B in which (a) said mixture in the gas or vapor phase is contacted with the first face of a membrane composed of (i) at least one active layer less than 100 micrometers in thickness comprising a solid adsorbent phase, selective for constituent A, dispersed in a non-porous, non-elastomeric polymer constituting a continuous phase and (ii) a porous support adhering directly to said at least one active layer, (b) the partial pressure of constituent A is kept lower at the second face of the membrane than at the first face and a mixture enriched in constituent A and impoverished in constituent B is collected on the second face of said membrane without a change in phase and (c) a mixture enriched in constituent B and impoverished in constituent A is collected on the first side of said membrane, a process wherein the thickness of the active layer is less than 100 micrometers and the ratio of the mass of the dispersed phase to the mass of the continuous phase in the active layer is greater than 1.

2. Process according to claim 1 wherein the adsorbent phase dispersed in the continuous polymer comprises a molecular sieve type zeolite.

3. Process according to claim 1 wherein the thickness of the active layer is less than 20 micrometers.

4. Process according to claim 1 wherein the thickness of the active layer is less than 1 micrometer.

5. A process according to claim 4 wherein the average size of the particles is less than 0.1 micrometer.

6. A process according to claim 5 wherein the ratio of the average size of particles of the dispersed adsorbent phase to the thickness of the active layer is less than 0.25.

7. A process according to claim 6 wherein the membrane is an asymmetric membrane obtained by coagulating said active layer by contacting an antisolvent with the first face of a viscous polymer film comprising the polymer solvent and the dispersed adsorbent phase under conditions such that only the face of said film becomes said active layer and resultant uncoagulated underlying film becomes porous and constitutes the support layer.

8. Process according to claim 1 wherein the solid adsorbent phase contains particles whose average size is less than 25 micrometers.

9. Process according to claim 1 wherein the average size of the particles is less than 0.1 micrometer.

10. Process according to claim 1 wherein the ratio of the average size of particles of the dispersed adsorbent phase to the thickness of the active layer is less than 0.25.

11. Process according to claim 1 wherein the membrane is an asymmetric membrane obtained by coagulating said active layer by contacting an anti-solvent with the first face of a viscous polymer film comprising the polymer solvent and the dispersed adsorbent phase under conditions such that only the face of said film becomes said active layer and resultant uncoagulated underlying film becomes porous and constitutes the support layer.

12. Process according to claim 1 wherein constituent A is hydrogen and constituent B is methane and wherein the dispersed adsorbent phase consists of a type 4A molecular sieve.

13. Process according to claim 1 wherein constituent A is methane and constituent B is water and wherein the dispersed adsorbent phase consists of a type 3A molecular sieve.

14. Process according to claim 1 wherein said mixture comprises n-paraffins and wherein the active layer comprises a type 5A molecular sieve, wherein the following combination is carried out:
(a) hydrogen in the vapor phase and the mixture are introduced into an isomerization zone, under isomerization conditions such that n-paraffins, isoparaffins and hydrogen are collected;
(b) the product in the vapor phase collected in this way is contacted with a first part of a separation zone, upstream from the membrane, and separation of n-paraffins, iso-paraffins and hydrogen is carried out by circulating, in a second part of said zone downstream from the membrane, at least a part of the hydrogen resulting from step (c) below;
(c) at the outlet of said first part, a second mixture of hydrogen and isoparaffins is collected, said second mixture is condensed and a fraction containing mainly isoparaffins on the one hand and hydrogen on the other is collected, which is recycled in the second part of the separation zone according to step (b);
(d) at the outlet of the second part of the separation zone, a third mixture rich in n-paraffins containing hydrogen is collected; and
(e) at least part of the third mixture is recycled in the isomerization zone according to step (a).

15. Process according to claim 1 wherein the non-elastomeric polymer is a polyimide.

16. A process according to claim 1 wherein the mixture to be separated comprises hydrogen and methane, the solid adsorbent phase is zeolite 4A and the non-elastomeric polymer is a polyimide.

17. A process according to claim 16 wherein the polyimide is a polyetherimide.

18. A process according to claim 1 wherein the mixture to be separated comprises normal pentane and isopentane, the solid adsorbent is zeolite 5A and the non-elastomeric polymer is a polyimide.

19. A process according to claim 18 wherein the polyimide is a polyetherimide.

20. A process according to claim 1 wherein said ratio is 2:1 to 6:1.

21. A process according to claim 1 wherein the non-porous continuous phase and the porous support are formed from the same non-elastomeric polymer.

22. A process according to claim 1, wherein the mixture to be separated comprises at least one hydrocarbon.

23. A membrane less than 100 microns in thickness composed of (a) at least one active layer comprising a solid adsorbent phase dispersed in a permeable non-porous, non-elastomeric polymer constituting a continuous phase and (b) a porous support adhering directly to said at least one active layer, the ratio of the mass of the dispersed phase to the mass of the continuous phase in the active layer being greater than 1.

24. A membrane according to claim 23 wherein the membrane is an asymmetric membrane obtained by coagulating said active layer by contacting an anti-solvent with the first face of a viscous polymer film comprising the polymer solvent and the dispersed adsorbent phase under conditions such that only the face of said film becomes said active layer and resultant uncoagulated underlying film becomes porous and constitutes the support layer.

25. A membrane according to claim 24 wherein the non-elastomeric polymer is a polyimide and the solid adsorbent phase is a zeolite.

26. A membrane according to claim 25 wherein the membrane is an asymmetric membrane obtained by coagulating said active layer by contacting an anti-solvent with the first face of a viscous polymer film comprising the polymer solvent and the dispersed adsorbent phase under conditions such that only the face of said film becomes said active layer and resultant uncoagulated underlying film becomes porous and constitutes the support layer.

27. A membrane according to claim 24, wherein said polymer is polyetherimide.

28. A membrane according to claim 23, wherein said ratio is 2:1 to 6:1.

29. A membrane according to claim 23, wherein said porous support is metallic.

30. A membrane according to claim 23, said porous support having pores of diameters greater than 25 microns.

31. A membrane according to claim 23, wherein the active layer is produced by suspending said solid adsorbent phase in a solvent solution of said polymer and a surfactant.

* * * * *